US006063119A

United States Patent [19]
Pintauro et al.

[11] Patent Number: 6,063,119
[45] Date of Patent: *May 16, 2000

[54] DEVICE FOR MAINTAINING URINARY CONTINENCE

[75] Inventors: William L. Pintauro, Ft. Lauderdale, Fla.; Rodney A. Brenneman, San Jaun Capistrano, Calif.; Mario Maciel, Pinon Hills, Calif.; Sheila K. Wallin, Irvine, Calif.

[73] Assignee: Galt Laboratories, Inc., Irvine, Calif.

[*] Notice: This patent is subject to a terminal disclaimer.

[21] Appl. No.: 09/098,396

[22] Filed: Jun. 17, 1998

Related U.S. Application Data

[63] Continuation of application No. 08/696,333, Aug. 13, 1996, Pat. No. 5,782,916.

[51] Int. Cl.[7] .................................................. A61F 2/04
[52] U.S. Cl. ................................................ 623/12; 600/29
[58] Field of Search ................................ 623/12; 600/29, 600/30

[56] References Cited

U.S. PATENT DOCUMENTS

| | | |
|---|---|---|
| 2,638,093 | 5/1953 | Kulick . |
| 3,797,428 | 3/1974 | Walsh et al. . |
| 3,812,841 | 5/1974 | Isaacson . |
| 3,863,622 | 2/1975 | Buuck . |
| 3,939,821 | 2/1976 | Roth . |
| 4,197,835 | 4/1980 | Reinicke . |
| 4,204,282 | 5/1980 | Bolt . |
| 4,222,377 | 9/1980 | Burton . |
| 4,408,597 | 10/1983 | Tenney Jr. . |
| 4,551,862 | 11/1985 | Haber . |
| 4,587,955 | 5/1986 | Gengler . |
| 4,679,546 | 7/1987 | Van Wallwijk et al. . |
| 4,705,518 | 11/1987 | Baker et al. . |
| 4,716,901 | 1/1988 | Jackson et al. . |
| 4,731,083 | 3/1988 | Fischell . |
| 4,784,660 | 11/1988 | Fischell . |
| 4,832,680 | 5/1989 | Haber . |
| 4,846,784 | 7/1989 | Haber . |
| 4,850,963 | 7/1989 | Sparks . |
| 4,878,889 | 11/1989 | Polyak . |
| 4,968,294 | 11/1990 | Salama . |

(List continued on next page.)

OTHER PUBLICATIONS

J. Gundian et al., "Mayo Clinic Experience with the AS800 Artificial Urinary Sphincter . . . ", *Urology*, 41:318–321 (1993).

R. Janknegt et al. "Electrically stimulated gracilis sphincter for treatment of . . . ", *Lancet*, 340:1129–1130 (1992).

M.D. Craggs et al., "A preliminary report on a new hydraulic sphincter for . . . ", *Journal of Medical Engineering & Technology*, 15:58–62 (1991).

O. Lukkarinen, et al., "Treatment of Urinary Incotinence with an Implantable . . . ", *Scand J. Urol Nephrol*, 23:85–88 (1989).

M. Abbar, et al., "Une revolution tranquille: l'endoprothese urethrale . . . ", *Progres en Urologie*, 3:771–777 (1993).

A. Gruneberger et al., "Entwicklung eines magnetischen Urethralverschlusses . . . ", *Zentralblatt fur Gynokologie* 115:328–331 (1993).

Summary of Dialog/Derwent World Pat. computer search, Mar. 17, 1995.

Summary of Dialog/Medline/Biosis/SciSearch/Embase computer search, Mar. 17, 1995.

(List continued on next page.)

*Primary Examiner*—Michael J. Milano
*Attorney, Agent, or Firm*—Knobbe, Martens, Olson & Bear LLP

[57] ABSTRACT

A prosthetic device for controlling urinary continence is disclosed. The device has an opening pressure that varies in response to changes in physiologic parameters. The device can be controlled by the patient voluntarily without manual intervention. A nonsurgical method of maintaining urinary continence is also disclosed.

17 Claims, 11 Drawing Sheets

U.S. PATENT DOCUMENTS

| | | |
|---|---|---|
| 4,994,019 | 2/1991 | Fernandez et al. . |
| 5,041,092 | 8/1991 | Barwick .................................... 600/29 |
| 5,064,434 | 11/1991 | Haber . |
| 5,088,980 | 2/1992 | Leighton . |
| 5,097,848 | 3/1992 | Schwartz . |
| 5,123,428 | 6/1992 | Schwartz . |
| 5,140,999 | 8/1992 | Ardito . |
| 5,197,984 | 3/1993 | Kedem . |
| 5,437,604 | 8/1995 | Kulisz et al. . |
| 5,476,434 | 12/1995 | Kalb et al. . |
| 5,509,889 | 4/1996 | Kalb et al. . |
| 5,634,878 | 6/1997 | Grundei .................................... 600/30 |
| 5,701,916 | 12/1997 | Kulisz ...................................... 600/29 |
| 5,711,314 | 1/1998 | Ardito ...................................... 600/29 |
| 5,782,916 | 7/1998 | Pintauro et al. . |
| 5,795,288 | 8/1998 | Cohen ....................................... 600/29 |
| 5,800,339 | 9/1998 | Salama ..................................... 600/29 |

OTHER PUBLICATIONS

Preliminary Prospectus: UroMed Corporation, Paine Webber Incorporated Vector Securities International, Inc. Jan. 24, 1994.

Brochure: *AMS Sphincter 800,* Urinary Prosthesis, Dry Facts of Incontinence Treatment, Pfizer American Medical Systems®, Jun. 1, 1991.

Brochure: HK Medical Technologies Incorporated, Autocath™ 100, 1994.

Stanton, S. et al., "The Mechanism of Continence", *Surgery of Female Incontinence,* 2d Ed. pp. 1–21, 1986.

DEVICE FOR MAINTAINING URINARY CONTINENCE

This is a Continuation of application Ser. No. 08/696,333, filed Aug. 13, 1996, now U.S. Pat. No. 5,782,916.

FIELD OF THE INVENTION

The present invention relates to the field of prosthetic urethral valves or seals for controlling urinary continence. More particularly, the present invention relates to a prosthetic urethral device having an opening pressure that varies in response to changes in physiologic parameters.

BACKGROUND OF THE INVENTION

Urinary incontinence is a widespread problem in the United States and throughout the world. Urinary incontinence affects people of all ages and can severally impact a patient both physiologically and psychologically. Urinary incontinence has a number of causes, including birth defects, disease, injury, aging, and urinary tract infection.

In light of the foregoing, a number of attempts have been made to combat urinary incontinence. One such attempt involves the use of a catheter connected to a collection bag with a clamping device on the catheter. Indwelling catheters, however, have a number of drawbacks. For instance, there is an infection risk associated with indwelling catheters, which provide a direct passage for bacteria or other microorganisms into the bladder. Thus, indwelling catheters can only be used for relatively short-term situations. In addition, indwelling catheters and associated collection bags are not cosmetically appealing to most patients.

Prosthetic urethral valves of the prior art for controlling incontinence also have numerous disadvantages. For instance, many prior art urethral valves utilize an inflatable cuff around the outside of the urethra. One disadvantage of such a valve is that it requires surgery for installation. In addition, such a valve must be operated externally and thus is dependent on manual intervention.

Intraurethral valves of the prior art also generally require manual intervention. Another problem associated with intraurethral valves is that they may be displaced into the bladder or expelled from the urethra. There is also an infection risk associated with many such valves since they extend into the meatus and/or have portions of the device external to the urethra providing a passage for microorganisms into the bladder.

Thus, there remains a need for a nonsurgically installed prosthetic urethral valve or seal that responds to physiological conditions and thus can be controlled voluntarily by the patient without manual intervention.

SUMMARY OF THE INVENTION

In one aspect of the present invention, there is provided a prosthetic urethral valve assembly. The valve assembly includes a tubular body having a proximal end, a distal end, and a central lumen extending therethrough. Attached to the proximal end of the tubular body is a first anchor. The first anchor conforms to a portion of the base of the bladder so that the prosthetic urethral valve assembly remains properly located relative to the bladder and the urethra. The valve assembly also includes a second anchor, which is attached to the tubular body at a point between the proximal end and the distal end of the tubular body. The second anchor lies within the urethra and helps to anchor the valve assembly therein. The valve assembly also includes a valve, which can be located within the lumen of the tubular body between the proximal end and the distal end of the tubular body. When positioned in the patient, the distal end of the tubular body is disposed in the midurethra, such as between the internal urethral sphincter and the external urethral sphincter so that the opening pressure of the valve varies in response to changes in physiologic parameters.

Another aspect of the present invention relates to a method of maintaining urinary continence in a patient. The method includes positioning the prosthetic urethral valve assembly of the present invention in a patient so that the distal end of the tubular body and preferably the valve lie in the midurethra, such as between the internal urethral sphincter and the external urethral sphincter so that the opening pressure of the valve varies in response to changes in physiologic parameters.

Another aspect of the present invention relates to a method of varying the opening pressure of a prosthetic urethral valve in response to changes in abdominal pressure. The method includes providing a prosthetic urethral valve having a proximal end, a distal end, and a valved flow path therebetween. The valve is positioned in a patient within the flow path between the bladder and the outside of the patient. Preferably, the valve is positioned in the patient within the urethra between the internal sphincter and the external sphincter. The method also includes exposing the distal side of the valve to elevations in intraabdominal pressure and increasing the opening pressure of the valve in response to elevations in intraabdominal pressure.

In accordance with another aspect of the present invention, there is provided a valveless intraurethral device or maintaining urinary continence. The valveless device includes a tubular body having a proximal end, a distal end, and a central lumen extending therethrough. Attached to the proximal end of the tubular body is a first anchor, which conforms to a portion of the base of the bladder so that the valveless device remains properly located relative to the bladder and the urethra. The valveless device is made of a substantially compliant material so that the tubular body of the device reversibly seals in response to internal forces affecting the urethra and bladder neck. For instance, when micturition is undesired, the tubular body of the valveless device reversibly seals in response to inwardly directed urethral forces, thereby maintaining urinary continence. The tubular body of the valveless device can also reversibly seal by kinking in response to rotational descent of the bladder neck and urethra, thereby maintaining continence, such as in patients suffering from incontinence caused by hypermobility and/or weak pelvic floor muscles.

DETAILED DESCRIPTION OF THE PREFERRED EMBODIMENT

Figure 1:
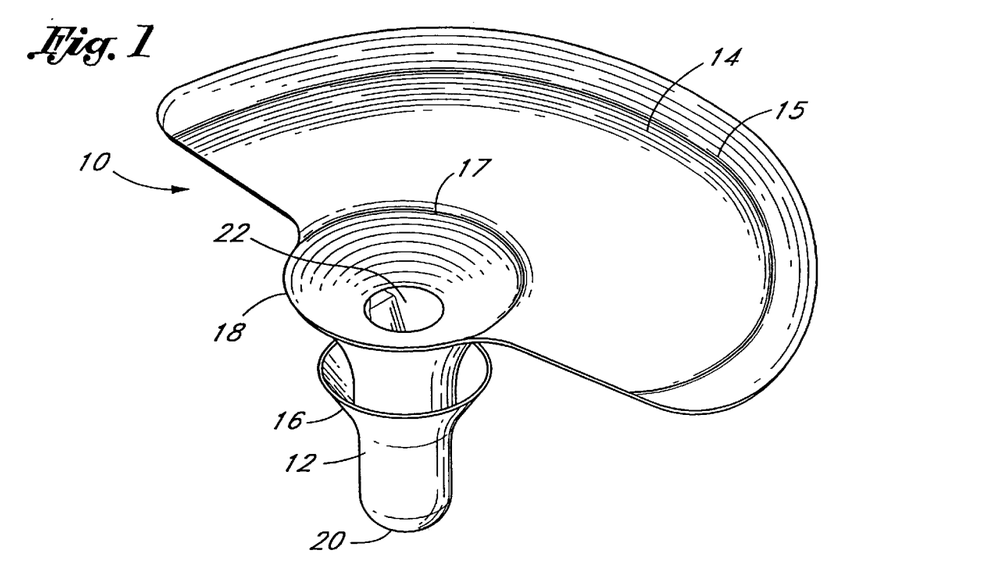
FIG. 1 is a perspective view of one embodiment of the prosthetic urethral valve according to the present invention.
Figures 2, 3:
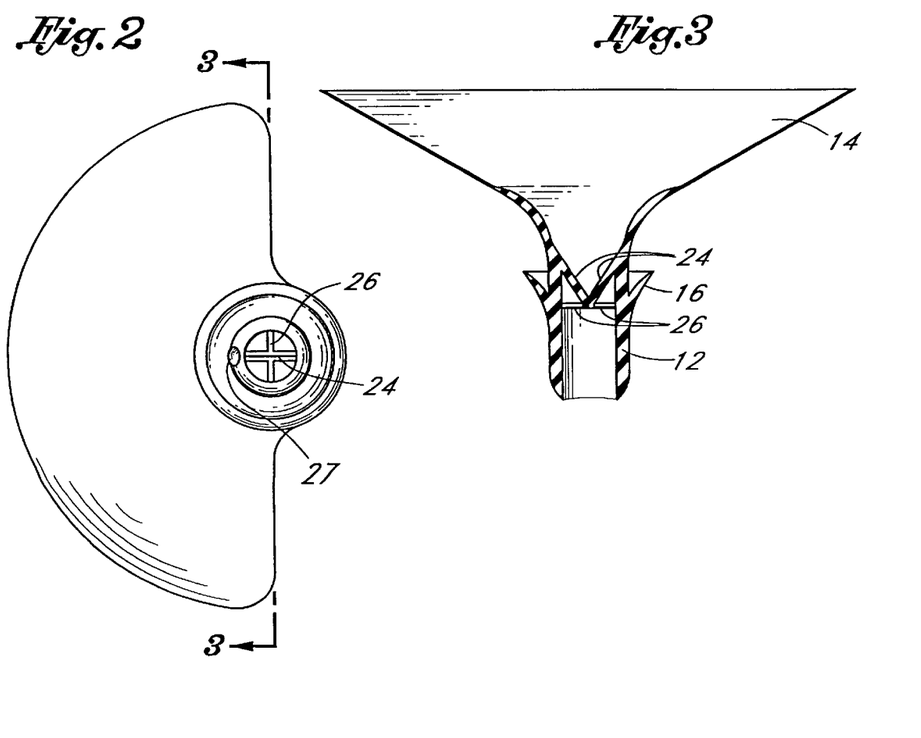
FIG. 2 is a bottom view of the valve depicted in FIG. 1.
FIG. 3 is an elevational cross-sectional view taken along line 3—3 of FIG. 2.

Referring to FIG. 1, there is disclosed a perspective view of the prosthetic urethral valve assembly 10 of the present invention. The valve assembly includes a tubular body 12 having a proximal end 18, a distal end 20, and a central lumen 22 extending therethrough. As illustrated in FIG. 2, a gripping tab or boss 27 is preferably included at the distal end 20 of tubular body 12 to facilitate transurethral placement of the valve, which is discussed in more detail below.

Figure 4:
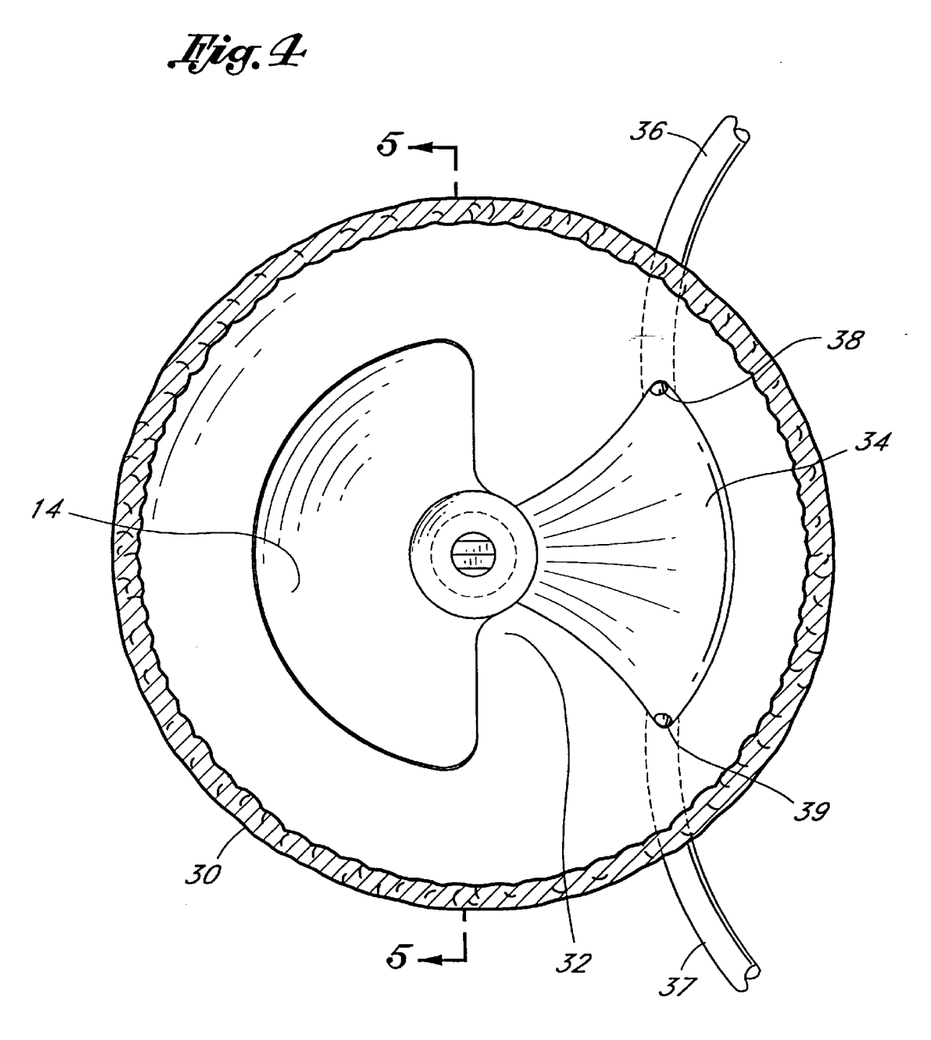
FIG. 4 is a transverse cross-sectional view through the bladder showing a top view of the device positioned in the bladder.
Figure 5:
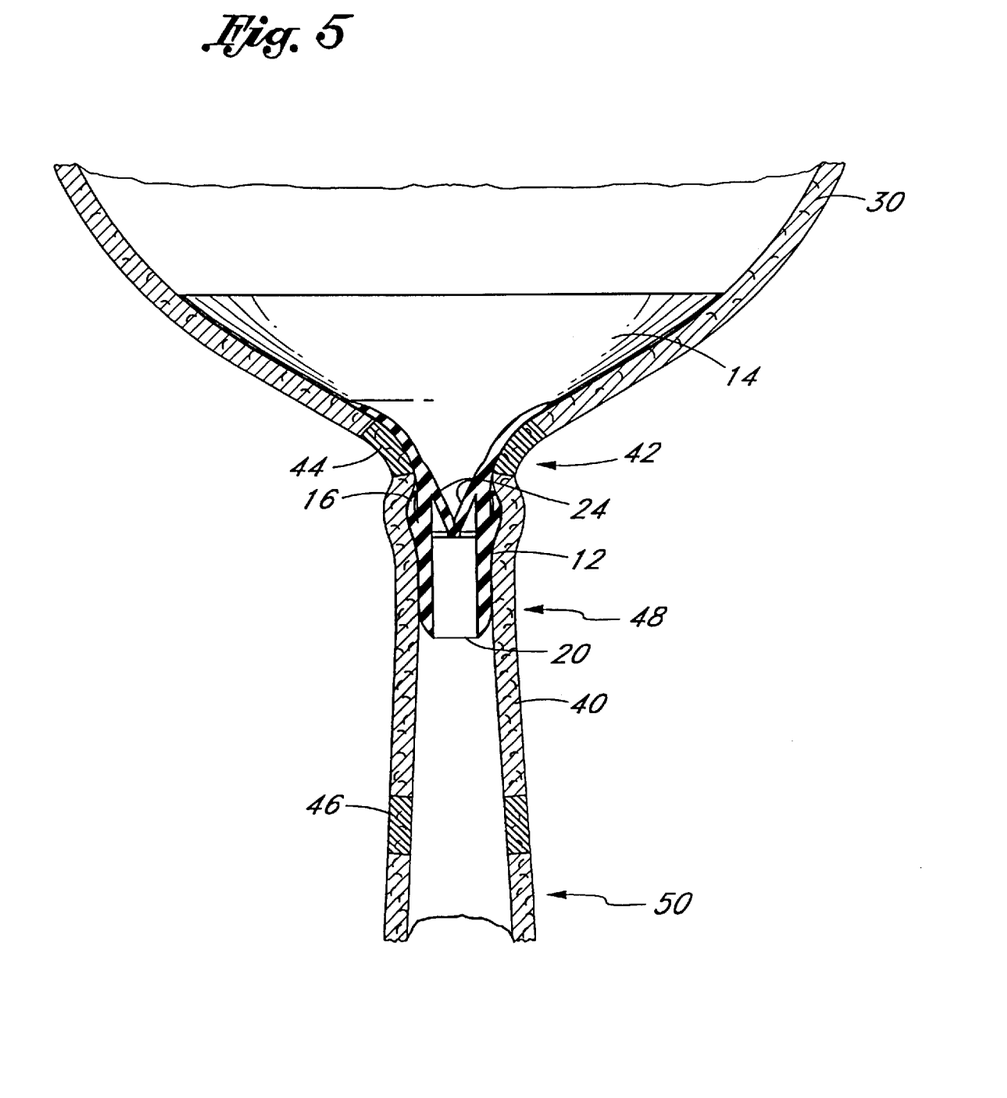
FIG. 5 is an elevational cross-sectional view taken along line 5—5 of FIG. 4.

The valve assembly 10 also includes a first anchor 14. The first anchor preferably conforms to a portion of a base 32 of a bladder 30 as illustrated in FIGS. 4 and 5. The first anchor 14 functions to releasably secure the valve assembly 10 relative to the bladder 30 and the urethra 40, while preferably avoiding contact with the trigone 34 of the bladder 30.

The trigone 34, illustrated in FIG. 4, is a triangular area of the bladder located between the urethra 40 and the two ureteric orifices 38 and 39. The ureteric orifices 38 and 39 drain urine from the ureters 36 and 37, respectively. Minimizing or avoiding contact between the first anchor 14 and the trigone 34 is desirable because the trigone contains a nerve bed which can be stimulated by tactile means resulting in an undesirable sense of urinary urgency.

In light of the foregoing considerations, the first anchor is preferably an atraumatic retention structure which is enlargeable from a first, collapsed configuration for transurethral placement to a second, enlarged configuration for resisting distal migration out of the bladder and into the urethra. In the illustrated embodiment, the first anchor comprises a pliable semiconical retention flap that inclines generally radially outwardly in the proximal direction from the proximal end 18 of the tubular body 12 as illustrated in FIG. 1. The retention flap is mechanically biased in the direction of the second, enlarged configuration as illustrated to help prevent the valve assembly 10 from being expelled distally from the urethra 40. The proximal surface of the first anchor 14 is exposed to the intravesical pressure of the bladder, which helps prevent the valve assembly 10 from being dislodged proximally into the central portion of the bladder.

In most patients, the trigone extends circumferentially approximately 60° to 90°. Thus, if properly placed within the bladder, the first anchor 14 can extend circumferentially up to as much as from approximately 270° to 300° and still avoid contacting the trigone. Preferably, the first anchor extends circumferentially either continuously or intermittently through an angle of approximately 100° to 180° in order to account for potential human error during placement, yet still provide an adequate surface area to achieve the anchoring function described above. In some embodiments, the construction material of the first anchor 14 is such that the anchoring function can be achieved with circumferential extension of less than about 100°.

A number of structures can be used to minimize either the circumference or the total contact area of the first anchor 14 yet still provide for adequate anchoring. For example, circumferentially extending reinforcing rings 15 and/or 17, such as a fine gauge spring wire may be incorporated into the valve assembly. The use of spring wires would provide a bias in the direction of the second, enlarged configuration while permitting a reduction in the size and mass of the anchor. Spring wires can alternatively extend in planes that are generally parallel to the longitudinal axis of the tubular body 12. Wires can be integrally molded into the anchor 14. Spring bias can also be optimized simply by adjusting the wall thickness of the anchor 14 and through appropriate materials choice.

In addition, as will be apparent to one of ordinary skill in the art, a variety of other structures could be used to accomplish the function of first anchor 14. For instance, the first anchor 14 may comprise a series of discontinuous, mechanically biased flexible struts extending from the proximal end 18 of the tubular body 12. Typically, two or three or more struts would be used. Alternatively, spring biased hinged anchors could be used to releasably secure the valve assembly 10 relative to the bladder 30 and the urethra 40.

In addition to the first anchor 14, preferably the valve assembly 10 also includes a second anchor 16. The second anchor 16 also helps to releasably secure the valve assembly 10 relative to the bladder 30 and the urethra 40. In addition, the second anchor 16 helps to stabilize the tubular body 12 within the urethra, especially in a patient having a large diameter urethra.

In the illustrated embodiment, the second anchor 16 is an annular flange attached to the tubular body 12 at a point between the proximal end 18 and the distal end 20. As illustrated in FIG. 1, the second anchor ramps radially outwardly in the proximal direction, thereby providing a mechanical bias against proximal dislodgement of the tubular body into the bladder. Optionally, one or more nitinol rings can be molded into the annular flange. After insertion of the valve assembly, expansion of the nitinol rings or other resilient support structures in response to body temperature provides an additional mechanical bias to help further secure the valve assembly.

As will be apparent to one of ordinary skill in the art, a variety of structures other than the proximally extending annular flange described above could be used to accomplish the function of second anchor 16. For instance, a variety of radially extending preferably atraumatic structures, such as semi-spheres, ridges or barbs can be attached to or integrally molded with the tubular body 12. Proximally and/or distally extending suture ends attached to the tubular body 12 using well known methods can also be used to accomplish the function of the second anchor 16.

The valve assembly 10 also includes a valve 24, such as a duckbill valve, which is preferably located within the fluid flow path through tubular body 12 between the proximal end 18 and the distal end 20. As illustrated in FIG. 3, optional valve supports 26 can also be included in the present invention to increase the opening pressure of the valve, if necessary, based on the characteristics of the material and dimensions used to construct the valve assembly 10.

The function of the valve is to assist normal physiological mechanisms to regulate the flow of urine through the tubular body 12. When the valve 24 is in an open position, the tubular body provides a fluid communication path between the bladder 30 and the urethra 40. When the valve is in the open position, preferably a flow rate of approximately 5–15 cc per second is achieved when the pressure differential on the valve is between approximately 20–30 $cmH_2O$. When the valve is in a closed position, the valve assembly 10 provides a seal preventing incontinence.

As will be apparent to one of ordinary skill in the art, a variety of structures other than the duck bill valve described above could be used to accomplish the function of the valve 24. For instance, the valve 24 could comprise a trap door type valve with an integral elastomeric return spring hinge or tether. Such a valve preferably has a relatively high opening pressure, such as from about 5–80 $cmH_2O$, and more preferably from about 5–20 $cmH_2O$, above which little resistance to flow is encountered. A multi-leaflet valve having struts to control baseline pressure or a poppet type valve having an integral elastomeric spring could also be used to accomplish the function of valve 24.

The opening pressure of the valve 24 depends on the type of valve chosen and the etiology of the patient's incontinence. The opening pressure of the valve, prior to being positioned within the patient, ranges from approximately 2–100 $cmH_2O$, more preferably from approximately 5–20 $cmH_2O$, and most preferably from approximately 5–10 $cmH_2O$. As discussed below, however, after the valve is properly positioned within the patient, the opening pressure of the valve varies in response to physiologic parameters.

Referring to FIG. 5, an elevational cross-sectional view of the valve assembly is shown positioned relative to the bladder 30 and the urethra 40. The urethra 40 is diagrammatically divided into a proximal portion 48 and a distal portion 50. An internal urethral sphincter 44 and an external urethral sphincter 46 are also shown. As illustrated in FIG. 5, the distal end 20 of tubular body 12 is located within the proximal portion 48 of the urethra 40 between the internal urethral sphincter 44 and the external urethral sphincter 46. Preferably, the valve 24 is also located in the proximal portion 48 of the urethra, although it can alternatively be positioned elsewhere along the flow path between the bladder 30 and the distal end 20 of the valve assembly 10. Optionally, a radiopaque material, such as gold, tantalum, or barium sulfate can be incorporated into the valve to ensure proper positioning. Preferably, the radiopaque material is incorporated as a visualization ring into the distal end 20 of the tubular body 12.

Figure 6:
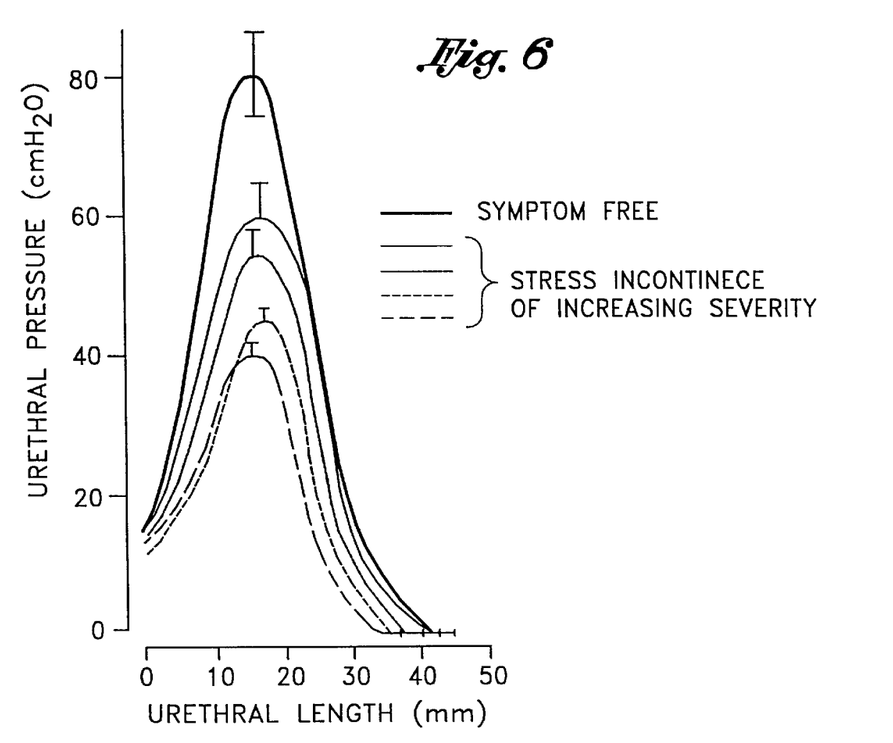
FIG. 6 graphically depicts the relationship between urethral pressure and urethral length in a group of symptom-free women and four groups with stress incontinence of varying severity.

Although knowledge of the physiology of the bladder and the urethra is incomplete, the external urethral sphincter is believed to be located approximately 1.0 to 4.0 cm, and more typically approximately 1.5 to 2.5 cm, distal to the bladderneck 42 in women, and approximately 5.0 to 6.0 cm distal to the bladderneck 42 in men. The external urethral sphincter is believed to primarily be responsible for the urethral pressure profile illustrated in FIG. 6. As can be seen in FIG. 6, urethral pressure is highest approximately 2 cm distal to the bladderneck. The inventors believe that in some instances the top portions of the curves illustrated in FIG. 6 may extend over a larger range of urethral length. In order to fully take advantage of the urethral pressure gradient, the valve 24 and the tubular body 12 preferably do not extend distal to the external urethral sphincter. More preferably, the tubular body 12 extends less than or equal to about 2.0 cm distal to the bladderneck. The relatively short length of the tubular body 12 allows the valve to be maximally exposed to the urethral pressure gradient, thereby aiding in keeping the valve 24 closed while the bladder is filling. During micturition, however, the urethra relaxes, removing this back pressure and aiding in the voiding process.

Figure 7A:
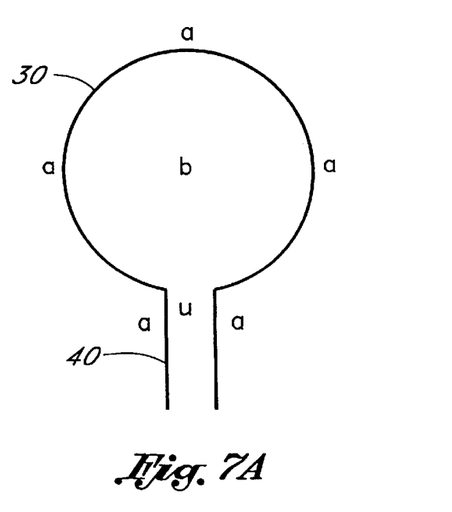
FIGS. 7A and 7B diagrammatically represent the bladder, the urethra, and various pressures relating to urinary tract physiology.
Figure 7B:
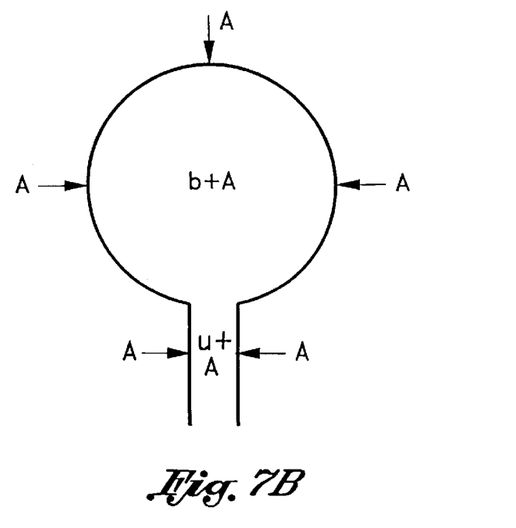

The urethral pressure gradient described above, also aids the valve assembly 10 in maintaining urinary continence during changes in physiologic parameters, such as increases in abdominal pressure caused by coughing. This aspect of the present invention is illustrated diagrammatically in FIGS. 7A and 7B. In FIGS. 7A and 7B, "a" equals resting intra-abdominal pressure, "b" equals resting bladder pressure, "u" equals resting urethral pressure, and "A" equals abdominal pressure rise on coughing. As can be seen in FIG. 7B, an increase in abdominal pressure increases both the bladder pressure and the urethral pressure. Because of the relatively short tubular body 12 of the present invention, however, the increase in urethral pressure caused by the increase in abdominal pressure is transmitted to the distal side of the valve 24, thereby momentarily increasing the effective opening pressure of the valve to help maintain valve closure during the increase in abdominal pressure.

In addition to the urethral pressure gradient described above, the bladderneck and the urethra also exert an inwardly directed force, which can enhance the function of the valve assembly 10 of the present invention. For instance, during bladder filling, the urethra exerts inwardly directed forces on the tubular body 12 and the valve 24, which help to keep the valve closed during the filling phase.

Conversely, during micturition, the pressure exerted by the bladderneck and the urethra decreases, thereby decreasing the radial force exerted on the tubular body and the valve. This decrease in radial force lowers the opening pressure of the valve and thus facilitates opening of the valve during micturition. Thus, although any of a variety of valve structures can be utilized in the valve assembly 10, valve structures which exhibit an increased opening pressure in response to radially inward compression are often preferred.

In contrast to the relatively short valve assembly 10 of the present invention, prosthetic urethral valve devices that extend into the meatus and/or have portions of the device external to the body are unable to take advantage of the urethral pressure gradient and radial forces described above.

Another advantage of the relatively short length of the valve assembly of the present invention is that it minimizes the risk of infection. In contrast, prosthetic urethral valve devices that extend into the meatus and/or have portions of the device external to the body provide a direct path for bacteria and other microorganisms to enter the urinary tract.

Referring to FIGS. 8–15, there is shown an alternate embodiment of the valve assembly of the present invention.

Figure 8:
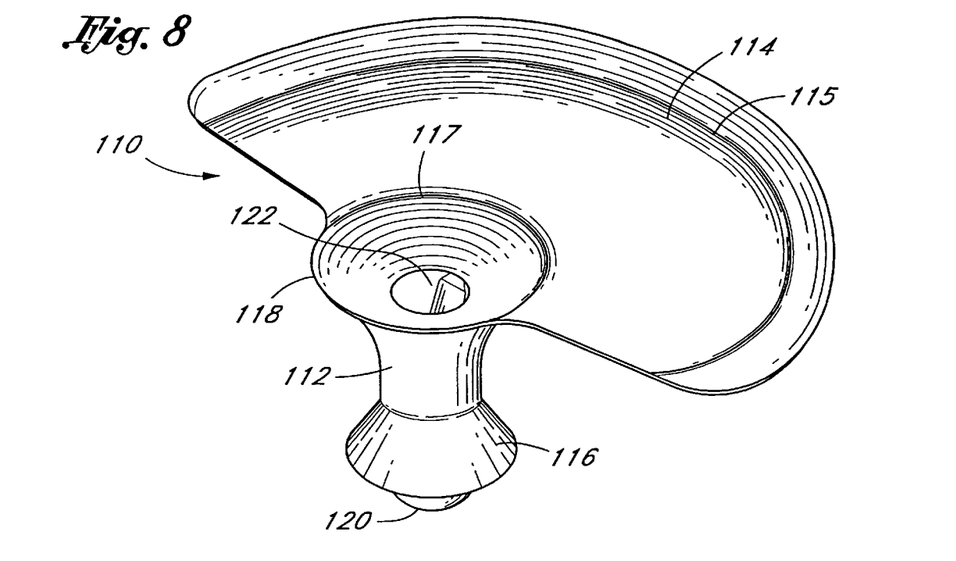
FIG. 8 is a perspective view of an alternate embodiment of the prosthetic urethral valve according to the present invention.

As illustrated in FIG. 8, the valve assembly 110 includes a tubular body 112 having a proximal end 118, a distal end 120 and a central lumen 122 extending therethrough. The valve assembly also includes a first anchor 114, a gripping boss 127, and reinforcing rings 115, 117.

In addition to the first anchor 114, preferably the valve assembly 110 also includes a second anchor 116. The illustrated second anchor 116 is an annular flange attached to the tubular body 112 at a point between the proximal end 118 and the distal end 120 of the tubular body. As illustrated in FIG. 8, the second anchor of the alternate embodiment preferably inclines distally from tubular body 112, thereby providing a mechanical bias against distal dislodgement of the valve assembly from the patent.

Figures 9, 10:
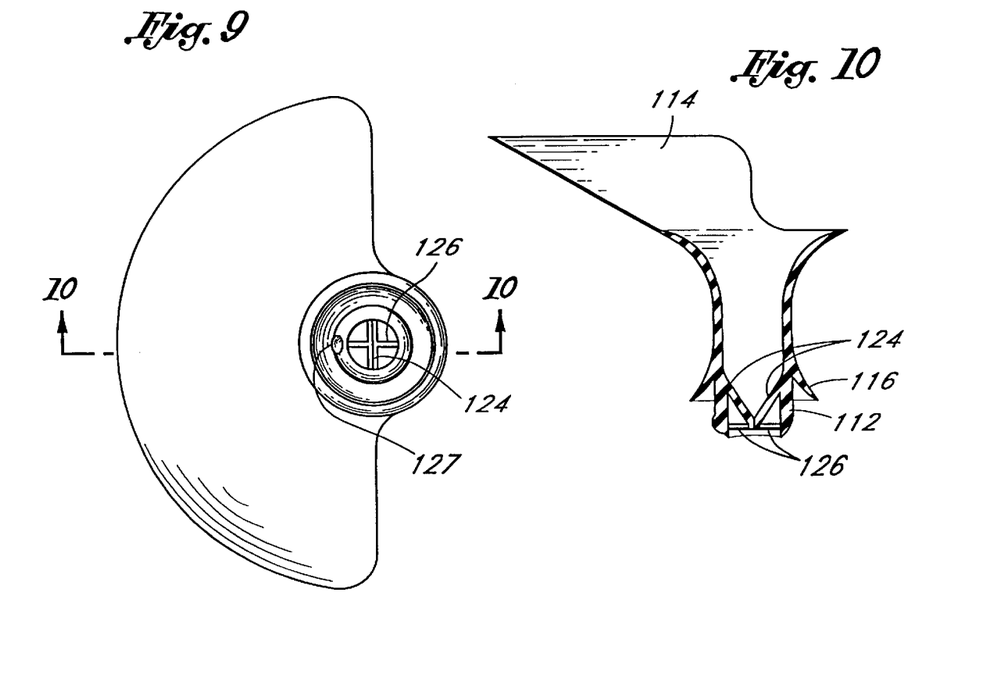
FIG. 9 is a bottom view of the valve depicted in FIG. 8.
FIG. 10 is an elevational cross-sectional view taken along line 10—10 of FIG. 9.
Figure 11:
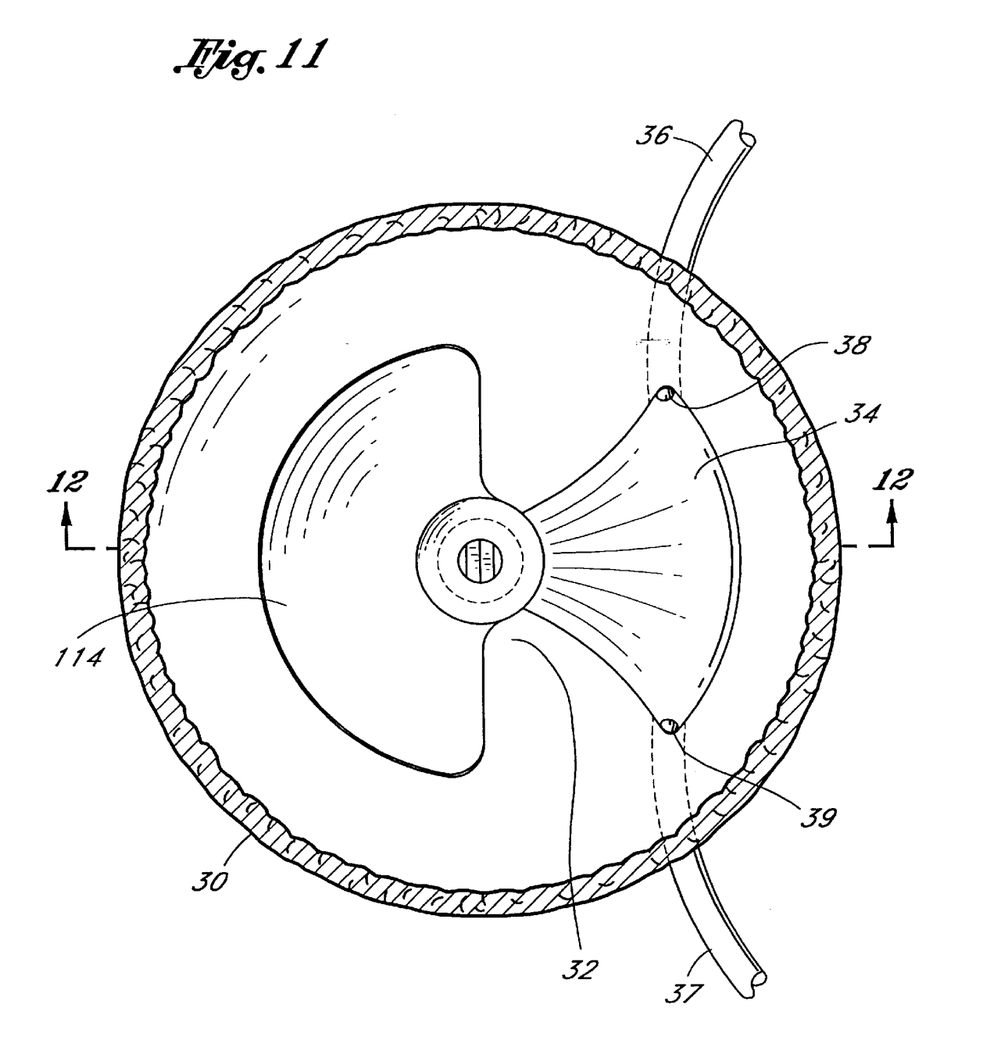
FIG. 11 is a transverse cross-sectional view through the bladder showing a top view of the alternate embodiment of the device positioned in the bladder.

The valve assembly 110 also includes a valve 124, such as a duckbill valve, which is preferably located within the lumen 122 of tubular body 112 between the proximal end 118 and the distal end 120 of the tubular body. As illustrated in FIG. 9, the orientation of valve 124 is preferably rotated approximately 90° relative to the valve depicted in FIG. 2. Thus, the coaptive edges of the two duckbill leaflets extend side to side when the valve is properly positioned in the patient. In addition, as illustrated in FIG. 10, optional valve supports 126 can be included to increase the opening pressure of the valve, if necessary, based on the characteristics of the material used to construct the valve assembly 110.

The length of the tubular body 112 of the valve assembly of the alternate embodiment is approximately the same as that of the valve assembly of FIGS. 1–5. As illustrated in FIG. 10, however, the distance between the valve 124 and the proximal end of the tubular body 112 of the alternate embodiment is greater than the distance between the valve 24 and the proximal end of the tubular body 12 of the valve assembly 10 illustrated in FIG. 3. Preferably the distance between the valve 124 and the proximal end of the tubular body is approximately 1.0–3.0 cm in the alternative embodiment, compared to approximately 0.5–2.0 cm in the embodiment of the valve 24 depicted in FIG. 3. The increased distance between the valve 124 and the proximal end of the tubular body in the alternate embodiment is especially useful in patients suffering from incontinence caused by hypermobility.

Figure 13:
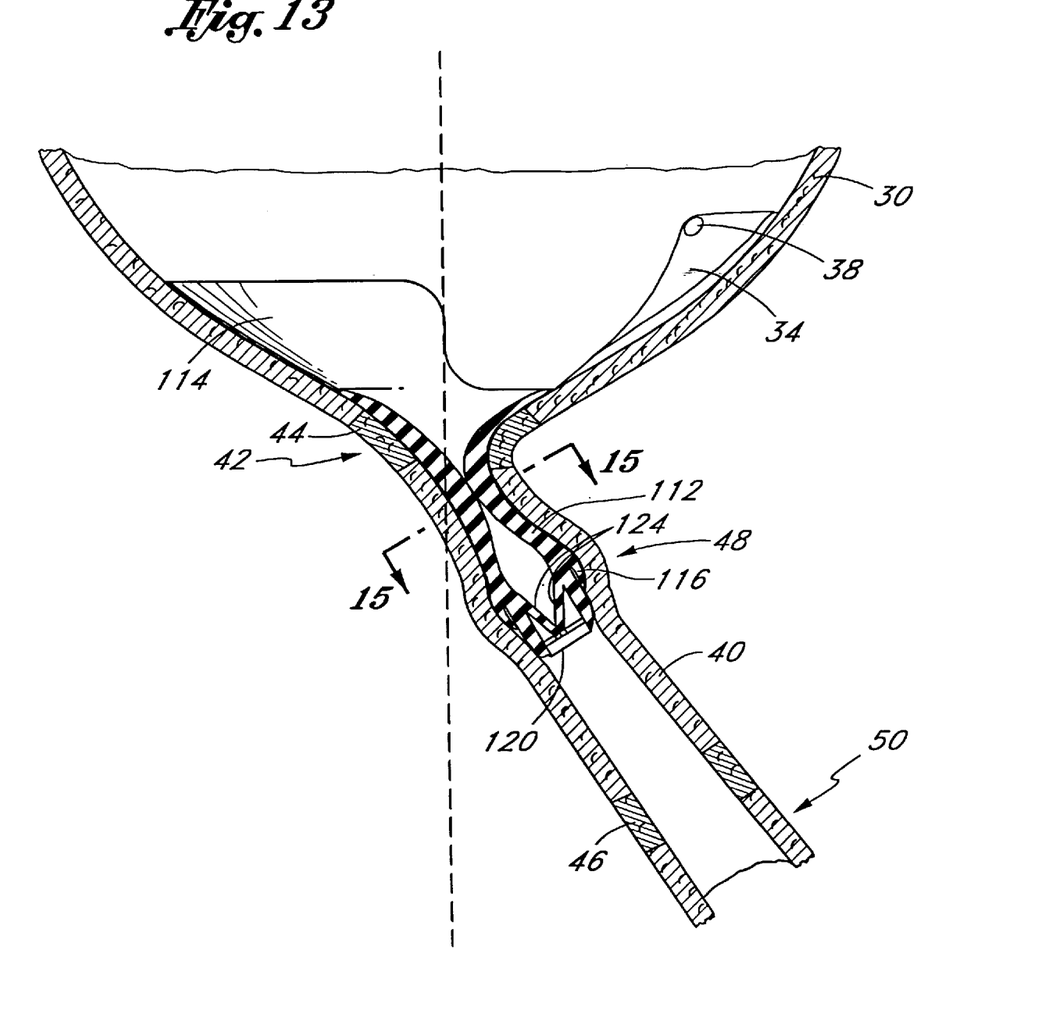
FIG. 13 illustrates the valve assembly of FIG. 12 during a hypermobility event.

In patients suffering from incontinence caused by hypermobility, the bladderneck and proximal urethra rotate and descend in response to increases in intra-abdominal pressure. During a hypermobility event, the orientation of the urethra relative to the bladder may change between approximately 20° and 90°. In such patients, rotation and descent of the bladderneck and urethra result in an uneven transmission of intra-abdominal pressure to the bladder and urethra. This can cause the bladder pressure to exceed the urethral pressure by as much as 100 cmH$_2$O, resulting in incontinence. As illustrated in FIG. 13, however, the increased distance between the valve 124 and the proximal end of the tubular body 112 of the alternate embodiment allows the tubular body to kink during a hypermobility event, thereby occluding the lumen of the tubular body, which helps prevent undesired leakage of urine through the valve assembly.

Figure 12:
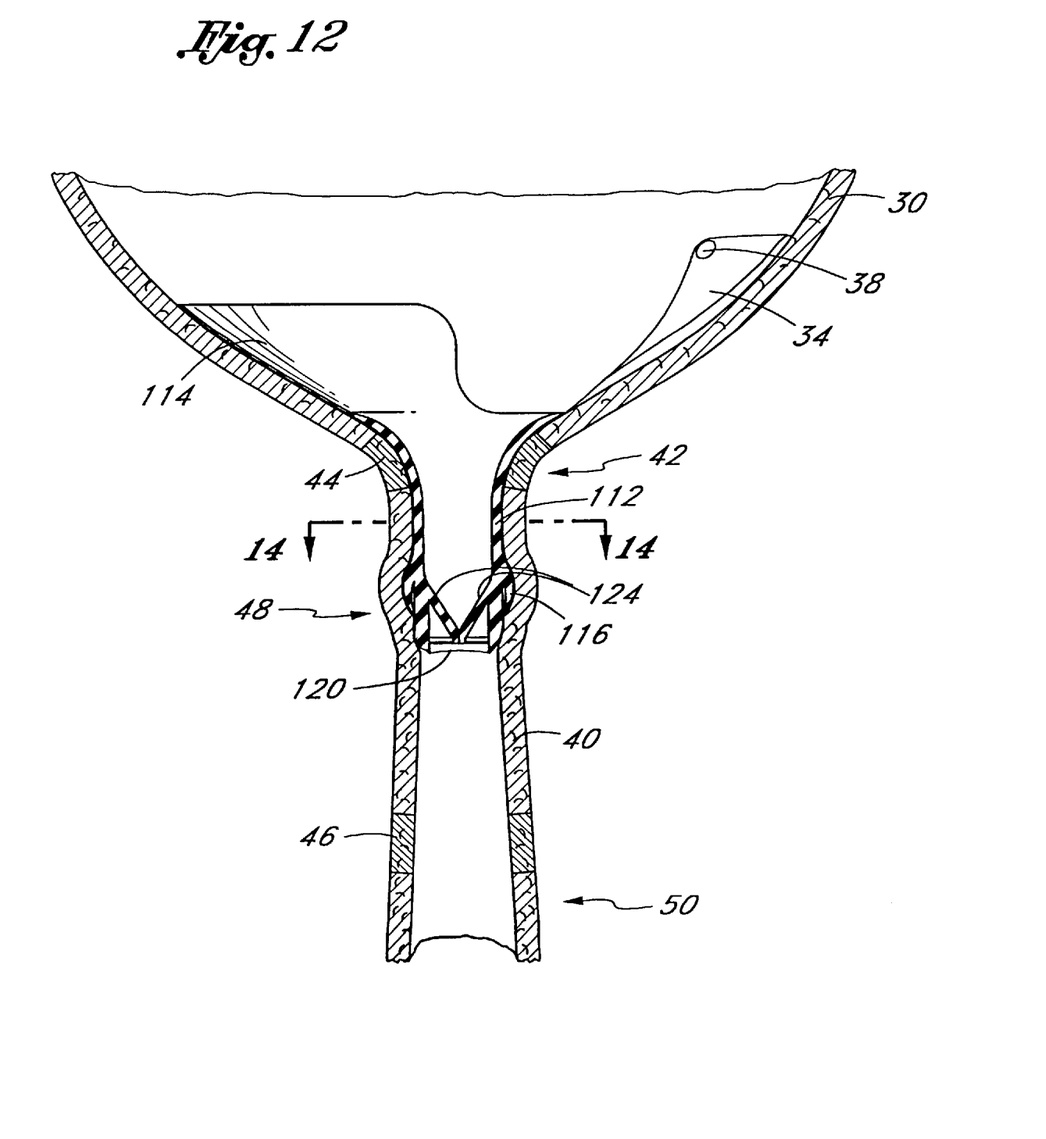
FIG. 12 is an elevational cross-sectional view taken along line 12—12 of FIG. 11.

FIGS. 12 and 13 illustrate the kinking feature of the tubular body 112 of the alternate embodiment of the present invention. FIG. 12 is an elevational cross-sectional view of the valve assembly positioned in the patient prior to a hypermobility event. In contrast, FIG. 13 illustrates the same view of the valve assembly during a hypermobility event. As can be seen, during the hypermobility event, the proximal portion of the tubular body 112 kinks or collapses, which helps to maintain continence without having to unduly increase the opening pressure of the valve 124.

Figure 14:
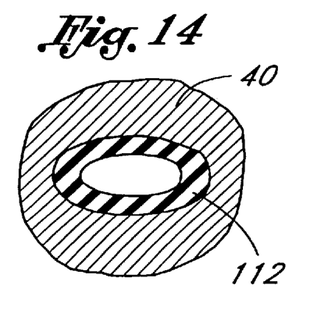
FIG. 14 is a cross-sectional view taken along line 14—14 of FIG. 12.
Figure 15:
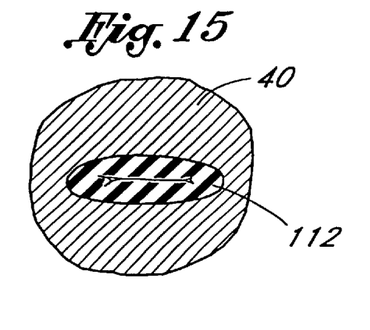
FIG. 15 is a cross-sectional view taken along line 15—15 of FIG. 13.

In order to facilitate kinking of the tubular body 112, the tubular body preferably has a thinner wall and/or a non-circular cross section, such as elliptical or oval, at the desired point of kinking. In many patients, such as those suffering from incontinence caused by hypermobility, the desired point of kinking would be in the proximal portion of the tubular body approximately 0.1–1.5 cm distal to the proximal end 118 of the tubular body. In some patients, however, the desired point of kinking may be located elsewhere along the tubular body 112 as will be evident to one of skill in the art. In addition, the device of the present invention may have a thinner wall and/or non-circular cross section throughout the length of the tubular body. A tubular body having a non-circular cross section is illustrated in FIGS. 14 and 15, which show the lumen of the tubular body before and after kinking of the tubular body caused by a hypermobility event.

As discussed earlier in connection with the valve assembly of FIGS. 1–5, one of ordinary skill in the art will recognize that a variety of structures other than the first anchor 114, second anchor 116, and valve 124 illustrated in FIGS. 8–13 could be used in accordance with the alternate embodiment of the present invention.

The valve assembly of the present invention can be manufactured using any of the variety of means known to those of ordinary skill in the art. Preferably the valve is injection molded into an integral unit. Alternatively, the valve assembly 10, 110 can be fabricated from two or more separately molded units, which are secured using conventional techniques such as thermal bonding, solvent bonding or suitable adhesives known in the art. For instance, the valve 24, 124 and the remainder of the valve assembly 10, 110 could be manufactured separately and then combined into a single unit using conventional methods known to those of ordinary skill in the art.

The device of the present invention may be made of any suitable resilient material which is biocompatible and resistant to a urine environment. Preferred materials include silicone rubbers, latex rubbers and polyurethane, with silicone rubbers being the most preferred. In addition to facilitating functioning of the device, the choice of soft, resilient materials also enhances patient comfort.

To minimize encrustation and infection, coatings well known to those of ordinary skill in the art, such as silver flouropolymers or sulfated polysaccharide pentosan-polysulfate, can be applied to the device.

The dimensions and configuration of the valve assembly 10, 110 can be varied considerably to suit particular design criteria desired for a particular application and still embody the present invention. Dimensions are largely limited by anatomical considerations as discussed above with respect to the length of the tubular body 12, 112, which is preferably approximately 0.5 cm to 3 cm in length, and more preferably less than about 1.5 cm in length. The diameters of the tubular body 12, 112 and second anchor 16, 116 are also dictated by anatomical considerations. In particular, the diameters of the tubular body and second anchor are chosen to fit securely within the urethra yet not exert an excess outward force on the urethra so that the tubular body can be compressed in response to urethral forces. Typical ranges for the outside diameter of the tubular body are approximately 0.5 cm to 0.8 cm (15–24 French), preferably about 0.6 cm (18 French). Typical ranges for the outside diameter of the second anchor are approximately 0.66 cm to 1 cm (20–30 French), preferably about 0.08 cm (24 French). The wall thickness of the tubular body is generally within the range of from about 0.15–3 mm, preferably about 0.25–1 mm, and more preferably about 0.4 mm.

In addition to anatomical considerations, the size and shape of various components of the valve assembly 10, 110 are also governed by the type of material used to construct the valve assembly.

A nonsurgical procedure for maintaining urinary continence in a patient, is generally accomplished as follows. A prosthetic urethral valve assembly such as 10 or 110 of the present invention is selected by the physician based on the sex of the patient as well as other anatomical and medical considerations. Using an installation device, such as the cystoscope 221 and grasping forceps 225 illustrated in FIG. 16 and described below, the physician transurethrally positions the prosthetic urethral valve assembly so that both the valve 24, 124 and the distal end 20, 120 of the tubular body 12, 112 lie between the internal urethral sphincter and the external urethral sphincter so that the opening pressure of the valve varies in response to changes in physiologic parameters.

Figure 16:
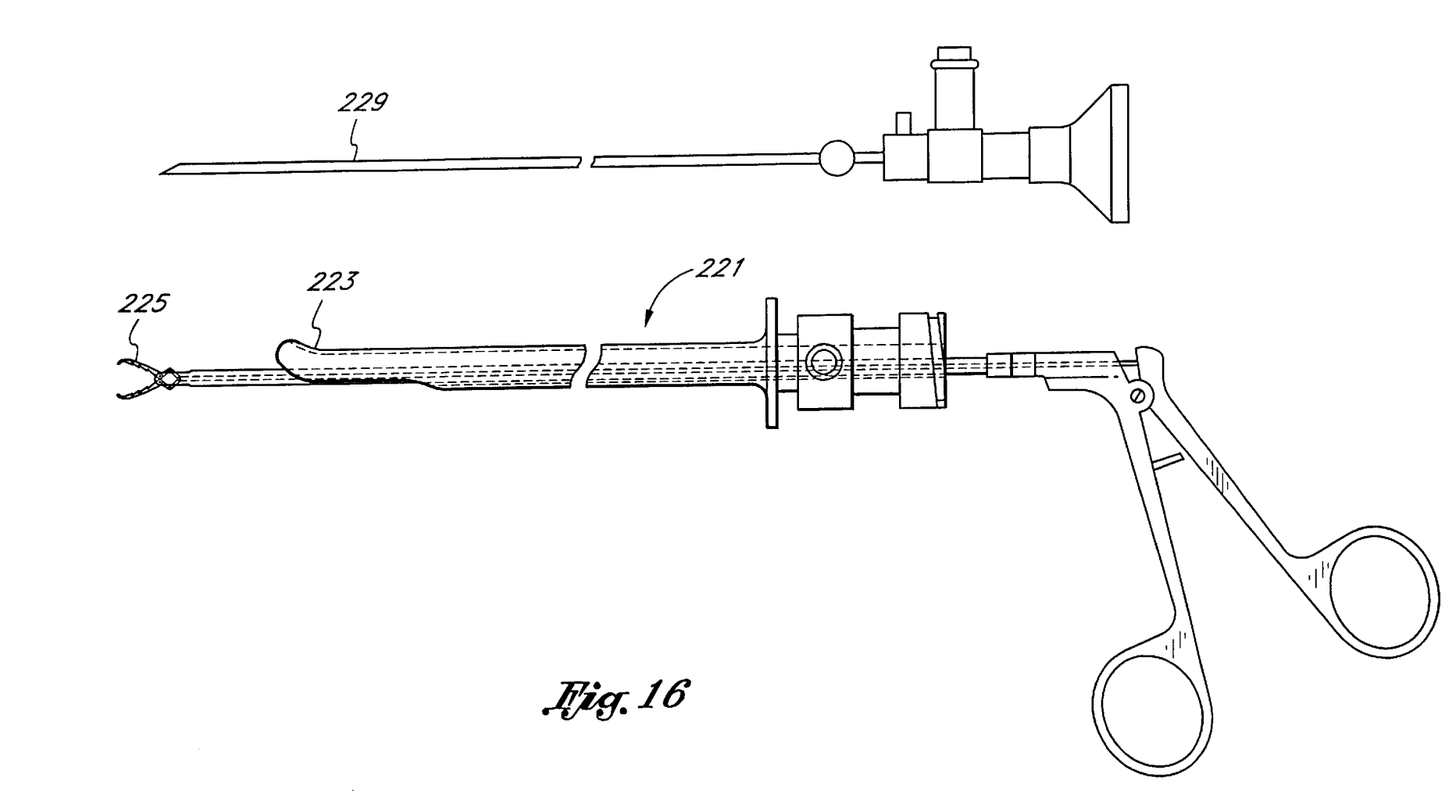
FIG. 16 is a partially exploded side view of various components of a device for installing the prosthetic urethral valve of the present invention.
Figure 17:
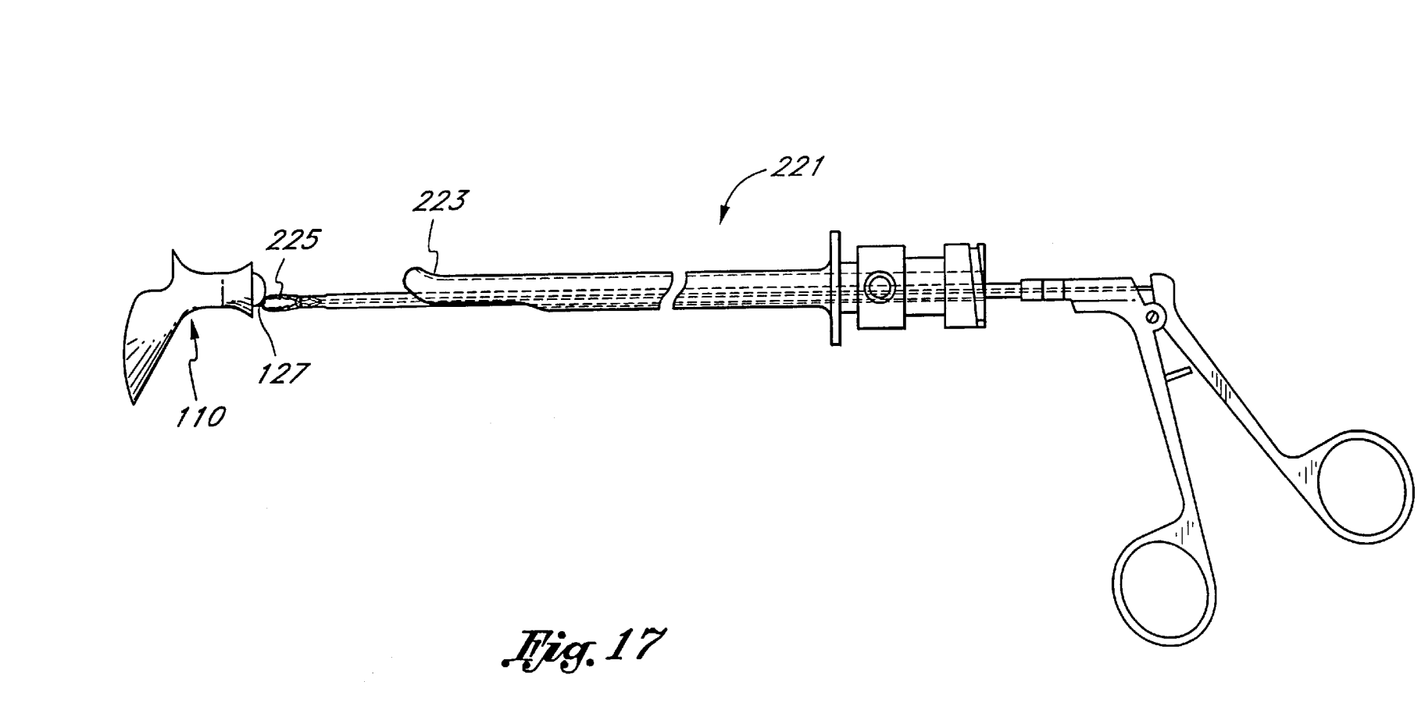
FIG. 17 is a side view of the grasping forceps extending distally from the cystoscope to releasably engage the prosthetic urethral valve of the present invention.

With reference to the installation device depicted in FIG. 16, one method of positioning the valve assembly 10, 110 is accomplished as follows. The physician transurethrally advances the cystoscope 221 and rod lens 229 into the bladder in accordance with conventional techniques. The physician then performs a standard cystoscopic examination of the bladder and fills the bladder with an irrigant. After performing the cystoscopic examination, the physician removes the cystoscope 221 from the urethra and removes the rod lens 229 from the cystoscope. The grasping forceps 225 are then passed through the cystoscope 221 so that the forceps 225 extend beyond the distal end 223 of the cystoscope 221 as illustrated in FIG. 16. A water soluble lubricant, such as K-Y jelly is applied to the outside of the valve assembly. The forceps 225 are used to releasably engage the valve assembly. For example, as illustrated in FIG. 17, the gripping boss 127 of the valve assembly is preferably releasably engaged by the forceps 225. The physician then carefully pushes the valve assembly into the distal end 223 of the cystoscope 221, collapsing the valve assembly as needed. The physician may also gently withdraw the forceps proximally to pull the valve assembly into the distal end of the cystoscope.

After placing the valve assembly 10, 110 into the distal end of the cystoscope, the physician passes the cystoscope through the urethra and into the bladder. Rod lens 229 is then inserted into the cystoscope 221 until it contacts the valve assembly. Using the rod lens and the forceps 225, the physician axially displaces the valve assembly distally out of the distal end 223 of the cystoscope 221 and into the bladder. While viewing the valve assembly 10, 110 in the bladder using the rod lens 229, the physician can rotate the forceps, if necessary, to properly orient the valve assembly and the first anchor 14, 114 relative to the base of the bladder and the trigone region.

While keeping the forceps stationary relative to the cystoscope, the physician withdraws the cystoscope, proximally thereby placing traction on the valve assembly in order to lodge the first anchor relative to the base of the bladder while avoiding contact between the first anchor and trigone region. Optionally, the position of the valve assembly can be confirmed using well known radiologic methods, such as in those embodiments in which a visualization ring has been incorporated into the valve assembly.

If the valve assembly is not properly positioned, the physician can readvance the cystoscope and the valve assembly into the bladder to rotate and reposition the valve. After the valve assembly is properly positioned, the physician releases the valve assembly from the forceps and withdraws the cystoscope, including the forceps and rod lens, from the patient.

The valve assembly 10, 110 can also be positioned using a standard embolectomy balloon catheter rather than the grasping forceps 225 described above. After performing a standard cystoscopic examination of the bladder and filling the bladder with an irrigant, the physician removes the cystoscope 221 from the urethra and removes the rod lens from the cystoscope leaving the bridge attached. The balloon catheter is then passed through the bridge and the cystoscope 221 so that the inflatable portion of the balloon catheter extends beyond the distal end 223 of the cystoscope. A water soluble lubricant, such as K-Y jelly, is applied to the outside of the valve assembly 10, 110. A standard balloon catheter threading tube is then advanced through the tubular body 12, 112 from the proximal end 18, 118 to the distal end 20, 120 of the tubular body.

The tip of the balloon catheter is then placed against the threading tube and the physician gradually extends both the balloon catheter and threading tube through the valve 24, 124 of the valve assembly 10, 110. The physician then carefully pushes the valve assembly into the distal end 223 of the cystoscope 221, collapsing the valve assembly as needed. After placing the valve assembly into the distal end of the cystoscope, the physician passes the cystoscope through the urethra and into the bladder.

The balloon catheter is then advanced distally so that the inflatable portion of the balloon catheter extends beyond the distal end of the cystoscope. The balloon is then inflated by the physician using conventional inflation media, such as fluid. The rod lens 229 is then inserted into the cystoscope 221 until it contacts the valve assembly. Using the rod lens (or other push rod structure), the physician axially displaces the valve assembly distally beyond the distal end of the cystoscope and into the bladder where it remains coaxially positioned about the balloon catheter shaft proximally of the balloon.

While viewing the valve assembly in the bladder using the rod lens, the physician can rotate the shaft of the balloon catheter, if necessary, to properly rotationally orient the valve assembly and the first anchor 14, 114 relative to the base of the bladder and the trigone region. During or after retraction of the cystoscope through the bladderneck, the physician retracts the inflated balloon catheter proximally in order to lodge the first anchor 14, 114 relative to the base of the bladder while avoiding contact between the first anchor and the trigone region. Optionally, the axial position of the valve assembly can be confirmed using well known radiologic methods, such as in those embodiments in which a visualization ring has been incorporated into the valve assembly. If the valve assembly is not properly positioned, the physician can readvance the cystoscope, balloon catheter, and valve assembly into the bladder to reposition the valve. After the valve assembly is properly positioned, the physician deflates the balloon catheter and withdraws the cystoscope, including the deflated balloon catheter and rod lens, from the patient.

Upon positioning internally as described above, the valve assembly 10 is automatically activated in response to physiologic conditions and thus can be controlled voluntarily by the patient without manual intervention.

As needed, the valve assembly 10, 110 can be removed from the patient and replaced with a new valve assembly. Removal of the valve assembly can be accomplished in a variety of ways, including through use of the cystoscope 221, rod lens 229, grasping forceps 225 and/or embolectomy balloon catheter described above. For example, the grasping forceps 225 are used to grasp the tab 27. The valve assembly can then be drawn into the distal end of a tubular structure such as a channel in the cystoscope 221. Preferably, the valve is drawn into the cystoscope while the cystoscope is simultaneously advanced in the distal direction to avoid pulling the first anchor through the bladderneck.

Alternatively, the valve assembly can be pushed distally from its installed position into the bladder, using the grasping forceps 225, rod lens 229 or other pushing structure. Preferably the physician will keep a grasp on the valve assembly such as by tab 27 using forceps 225 throughout the proximal displacement step. Once the valve assembly is in the bladder, it can be pulled into the end of the cystoscope. With certain anchor designs, the anchor may simply be pulled transurethrally from the patient.

Figure 18:
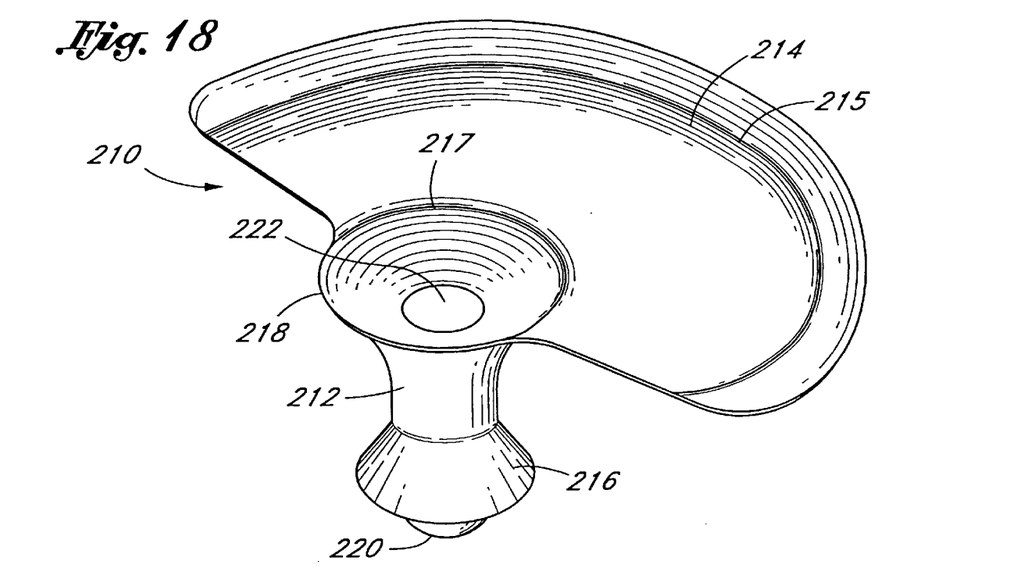
FIG. 18 is a perspective view of valveless embodiment of the device according to the present invention.
Figures 19, 20:
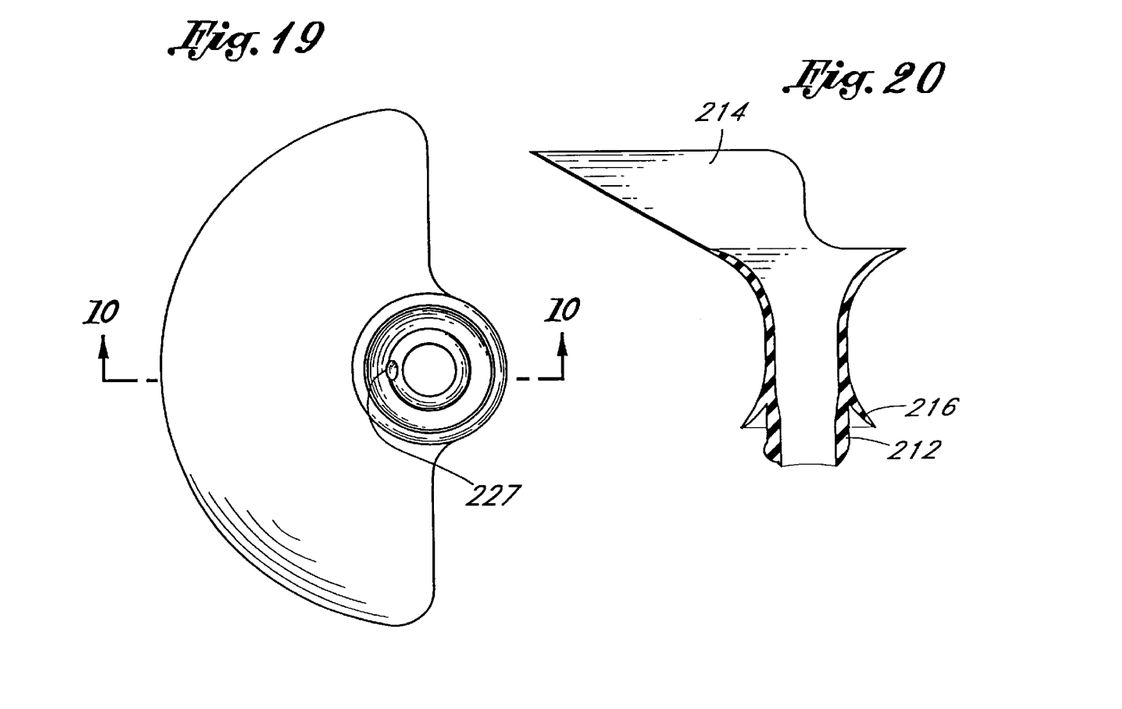
FIG. 19 is a bottom view of the valveless embodiment depicted in FIG. 18.
FIG. 20 is an elevated cross-sectional view taken along line 20—20 of FIG. 19.

Referring to FIGS. 18–20, there is shown a valveless embodiment of the present invention. The valveless device 210 includes a tubular body 212 having a proximal end 218, a distal end 220 and a central lumen 222 extending therethrough. The valveless device also includes a first anchor 214, a gripping boss 227 and reinforcing rings 215, 217.

In addition to the first anchor 214, the valveless device may also include a second anchor 216. The structure and function of the second anchor 216 illustrated in FIGS. 18–20 is generally similar to that of the previously described embodiments of the present invention.

The valveless device 210 functions as a bulking agent, which reversibly seals in response to the previously described inwardly directed urethral forces. These forces on the urethra help to seal the tubular body when micturition is undesired, thereby maintaining urinary continence. Conversely, when micturition is desired, the pressure exerted by the urethra and bladderneck decreases, thereby allowing the tubular body to open.

The tubular body 212 of the valveless device 210 can also function as a reversible seal by kinking in response to the previously described rotational descent of the bladderneck and urethra, such as during a hypermobility event.

The dimensions and configuration of the valveless device 210 are generally similar to those of the previously described embodiment illustrated in FIGS. 8–15. The tubular body 212 may be longer and have a thicker wall, however, in order to enhance the valveless device's ability to serve as a bulking agent, yet still take advantage of the urethral pressure gradient and other previously discussed aspects of urinary anatomy/physiology.

Typical ranges for the length of the tubular body 212 of the valveless device 210 are approximately 1.0–3.0 cm, preferably about 1.0–2.0 cm. Typical ranges for the outside diameter of the tubular body 212 and second anchor 216 are generally similar to those of the previously described embodiments of the present invention. Typical ranges for the wall thickness of the tubular body of the valveless device are approximately 0.15–3 mm, preferably about 0.4–1.5 mm, and more preferably about 0.4 mm. The tubular body of the valveless device can also have a variable thickness wall as previously discussed, wherein the wall of the proximal portion of the tubular body is thinner than that of the distal portion to facilitate kinking of the proximal portion, such as a during a hypermobility event. In addition, as previously discussed, in order to facilitate kinking, the tubular body can have a non-circular cross section, such as elliptical or oval, at the desired point of kinking or throughout the length of the tubular body.

As will be apparent to one of skill in the art, the valveless embodiment can be manufactured in accordance with any of a variety of techniques and materials, such as those previously described. Also as discussed above, in addition to anatomical considerations, the size and shape of various components of the valveless device are governed by the type of material used to construct the device. For instance, particularly compliant materials, such as the silicone rubbers and other materials described above, facilitate urethral compression and/or kinking of the tubular body of the device, especially in devices having a thicker walled tubular body.

As with the previously described embodiments of the present invention, one of ordinary skill in the art will recognize that a variety of structures other than the first anchor 214 and second anchor 216 could be used in accordance with the valveless embodiment. One of ordinary skill in the art will also recognize that any of a variety of installation and removal techniques, including those described above, could be used to position the valveless device within the urinary tract of the patient and/or to remove the device therefrom.

Although this invention has been described in terms of certain preferred embodiments, other embodiments which will be apparent to those of ordinary skill in the art in view of the disclosure herein are also within the scope of this invention. Accordingly, the scope of the invention is intended to be defined only by reference to the appended claims.

What is claimed is:

1. A urethral prosthesis, comprising:
   a tubular body having a proximal end, a distal end, and a lumen therein; and
   a valve located within the lumen between the proximal end and the distal end of the tubular body;
   wherein the opening pressure of the valve varies in response to internal forces affecting at least one of the urethra and bladder neck.

2. The urethral prosthesis of claim 1, wherein the prosthesis is made of a substantially resilient material so that the tubular body reversibly seals in response to internal forces affecting at least one of the urethra and bladder neck.

3. The urethral prosthesis of claim 1, further comprising a gripping tab at the distal end of the tubular body to facilitate transurethral placement and removal of the prosthesis.

4. The urethral prosthesis of claim 1, wherein the valve is a duckbill valve having a first and second coaptive leaflets.

5. The urethral prosthesis of claim 4, further comprising a first valve support member extending between the tubular body and the first leaflet and a second valve support member extending between the tubular body and the second leaflet to increase the opening pressure of the duckbill valve.

6. The urethral prosthesis of claim 1, further comprising a radiopaque material incorporated into the prosthesis to facilitate visualization of the prosthesis in the patient.

7. The urethral prosthesis of claim 1, wherein at least a portion of the tubular body has a non-circular cross-section.

8. The urethral prosthesis of claim 1, wherein the wall of the tubular body has a non-uniform thickness.

9. The urethral prosthesis of claim 1, wherein the length of the tubular body is less than the length of the urethra.

10. A method of maintaining urinary continence in a patient, comprising the steps of:

providing a urethral prosthesis having a proximal end and a distal end and an obstructable flow path extending at least part way therethrough; and positioning said prosthesis in the patient so that both the proximal end and the distal end of the tubular body lie in the urethra or bladder and the obstruction of the flow path varies in response to internal forces affecting at least one of the urethra and bladder neck.

11. The method of claim 10, wherein the prosthesis includes a radiopaque material, and wherein the positioning step further comprises confirming the position of the prosthesis using the radiopaque material.

12. A method of imposing and removing an obstruction to flow in the urethra in response to change in abdominal pressure, comprising the steps of:

providing a urethral prosthesis having a proximal end, a distal end and an obstructable flow path therebetween;

positioning the prosthesis in a patient such that at least a portion of the flow path is positioned within the urethra between the internal sphincter and the external sphincter;

exposing the flow path to elevations in intraabdominal pressure; and increasing the opening pressure of the prosthesis in response to elevations in intraabdominal pressure.

13. The method of claim 12, wherein the prosthesis includes a radiopaque material, and wherein the positioning step further comprises confirming the position of the prosthesis using the radiopaque material.

14. A method of maintaining urinary continence in a patient comprising the steps of:

providing a urethral prosthesis having an obstructable flow path therein; and positioning said prosthesis in the patient so that the flow path is positioned in between an internal urethral sphincter and an external urethral sphincter, so that the opening pressure of the obstructable flow path varies in response to internal forces affecting at least one of the urethra and bladder neck.

15. A urethral prosthesis, comprising:

a tubular body having a proximal end, a distal end, and a central lumen therein; and an obstructable flow path within the lumen between the proximal end and the distal end of the tubular body;

wherein the opening pressure of the flow path varies in response to internal forces affecting at least one of the urethra and bladder neck.

16. A method of maintaining urinary continence in a patient, comprising the steps of:

providing a urethral prosthesis having a proximal end and a distal end and an obstructable flow path therein; and positioning said prosthesis in the patient so that at least one of the proximal end and the distal end of the tubular body lie in the urethra or bladder and the obstruction of the flow path varies in response to internal forces affecting at least one of the urethra and bladder neck.

17. A method of maintaining urinary continence in a patient comprising the steps of:

providing a urethral prosthesis having an obstructable flow path; and positioning said prosthesis in the patient so that the flow path extends through the midurethra, in between an internal urethral sphincter and an external urethral sphincter, so that the opening pressure of the obstructable flow path varies in response to internal forces affecting at least one of the urethra and bladder neck.

* * * * *